(12) United States Patent
Kiel et al.

(10) Patent No.: US 6,869,618 B2
(45) Date of Patent: Mar. 22, 2005

(54) PROCESS FOR PREPARING TANNATE LIQUID AND SEMI-SOLID DOSAGE FORMS

(75) Inventors: Jeffrey S. Kiel, Gainesville, GA (US); H. Greg Thomas, Villa Rica, GA (US); Narasimhan Mani, Gainesville, GA (US)

(73) Assignee: Kiel Laboratories, Inc., Gainesville, GA (US)

( * ) Notice: Subject to any disclaimer, the term of this patent is extended or adjusted under 35 U.S.C. 154(b) by 0 days.

(21) Appl. No.: 10/119,285

(22) Filed: Apr. 9, 2002

(65) Prior Publication Data

US 2003/0050252 A1 Mar. 13, 2003

Related U.S. Application Data

(60) Provisional application No. 60/282,969, filed on Apr. 10, 2001.

(51) Int. Cl.$^7$ .......................... A61K 9/14; A01N 25/00; A01N 33/02; A01N 43/40
(52) U.S. Cl. ...................... 424/489; 514/849; 514/850; 514/853; 514/855; 514/937; 514/653; 514/352
(58) Field of Search ..................... 424/489; 514/849, 514/850, 853, 855, 937, 653, 352

(56) References Cited

U.S. PATENT DOCUMENTS

| | | | |
|---|---|---|---|
| 2,950,309 A | 8/1960 | Cavallito | |
| 3,282,789 A | 11/1966 | Marty et al. | |
| 4,309,989 A | 1/1982 | Fahim | |
| 4,552,899 A | 11/1985 | Sunshine et al. | |
| 4,619,934 A | 10/1986 | Sunshine et al. | |
| 4,749,697 A | 6/1988 | Sunshine et al. | |
| 4,749,711 A | 6/1988 | Sunshine et al. | |
| 4,749,721 A | 6/1988 | Sunshine et al. | |
| 4,749,722 A | 6/1988 | Sunshine et al. | |
| 4,749,723 A | 6/1988 | Sunshine et al. | |
| 4,767,402 A | 8/1988 | Kost et al. | |
| 4,839,354 A | 6/1989 | Sunshine et al. | |
| 5,025,019 A | 6/1991 | Sunshine et al. | |
| 5,164,398 A | 11/1992 | Sims et al. | |
| 5,599,846 A | * 2/1997 | Chopdekar et al. | |
| 5,614,178 A | 3/1997 | Bloom et al. | |
| 5,663,415 A | * 9/1997 | Chopdekar et al. | |
| 5,759,579 A | 6/1998 | Singh et al. | |
| 6,037,358 A | 3/2000 | Gordziel | |
| 6,063,770 A | 5/2000 | Falcon | |
| 6,117,452 A | 9/2000 | Ahlgren et al. | |
| 6,187,315 B1 | 2/2001 | Falcon | |
| 6,287,597 B1 | * 9/2001 | Gordziel | |
| 6,306,904 B1 | * 10/2001 | Gordziel | |

OTHER PUBLICATIONS

Ronald J. Goldberg, M.D.; Franklin I. Shuman, M.D., "Evaluation of a Prolonged Action Oral Antihistaminic Preparation as Treatment for Allergic Disorders," Clinical Reports, 1st ed., Clinical Medicine (United States), vol. 72 (No. 9), p. 1475–1479, (Sep. 1, 1965).

John M. Weiler, M.D.; et al, "Randomized, double–blind, parallel groups, placebo–controlled study of efficacy and safety of Rynatan in the treatment of allergic rhinitis using an acute model," Annals of Allergy, Academy of Clinical Allergy & Immunology (ACAI), (United States), vol. 64 (No. 1), p. 63–67, (Jan. 1, 1990).

DSC Laboratories, "Pharmaceutical Medicine Insert for Phenylephrine Tannate/Pyrilamine Tannate Suspension," DSC Laboratories (Muskegon, MI), (Aug. 1, 2001).

Cypress Pharmaceutical, Inc., "Pharmaceutical Medicine Insert for R–TANNIC–S A/D (phenylephrine tannate, pyrilamine tannate suspension)," Cypress Pharmaceutical, Inc. (Madison, MS), (Mar. 1, 2001).

* cited by examiner

Primary Examiner—Thurman K. Page
Assistant Examiner—Humera N. Sheikh
(74) Attorney, Agent, or Firm—King & Schickli, PLLC

(57) ABSTRACT

An active ingredient from the group of an antihistamine, a decongestant, an antitussive or anticholinergic is dissolved in a suitable solvent and added to a dispersion of tannic acid in water to form the tannate salt complex of the active ingredient. The active ingredient tannate salt complex without isolation or purification is then added to a liquid or semi-solid medium composed of thickening, suspending, coloring, sweetening and flavoring agents, with stirring. Thereafter, preservatives, pH-adjusting and anti-caking agents in a suitable solvent are mixed with the liquid or semi-solid medium to generate a therapeutic dosage form.

9 Claims, No Drawings

US 6,869,618 B2

PROCESS FOR PREPARING TANNATE LIQUID AND SEMI-SOLID DOSAGE FORMS

This application claims the benefit of U.S. Provisional Patent Application Ser. No. 60/282,969, filed Apr. 10, 2001, the disclosure of which is incorporated herein by reference.

BACKGROUND OF THE INVENTION

1. Field of the Invention

The present invention relates generally to the field of tannate chemistry and more specifically to methods for processing tannate suspensions.

2. Description of the Prior Art

The use of tannate suspensions for pharmaceutical use is well-known. U.S. Pat. No. 6,287,597 describes tannate suspensions containing pyrilamine tannate and phenylephrine tannate. The suspension is prepared in a conventional manner such that one teaspoon contains 30 mg pyrilamine tannate and 5 mg phenylephrine tannate with benzoic acid, coloring agent, natural and artificial flavors, glycerin, kaolin, magnesium aluminum silicate, methyl paraben, pectin, purified water, saccharin, sodium hydroxide and sucrose or sorbitol. The January 1990 issue of *Annals of Allergy*, Volume 64, describes combinations of chlorpheniramine tannate, pyrilamine tannate and phenylephrine tannate. An article in *Clinical Medicine*, dated September 1965, pages 1475–1478 describes tablets of pyrilamine tannate, chlorpheniramine tannate and amphetamine tannate. Phenylephrine tannate compositions are disclosed in U.S. Pat. No. 5,599,846 and phenylephrine tannate and chlorpheniramine tannate compositions are disclosed in U.S. Pat. No. 6,037,358. None of these references suggest or describe the production of a suspension by means of an in-situ conversion to the tannate salt of the active ingredient to provide a dosage form which affords a sustained release of the active ingredient over prolonged intervals of time. Such a suspension is needed to improve patient compliance with dosage requirements.

SUMMARY OF THE INVENTION

The present invention provides a manufacturing process for in-situ conversion and incorporation thereof, of tannate salt complexes of antihistamine, antitussive, decongestant and anticholinergic class of pharmaceutical compounds into a sustained release therapeutic liquid or semi-solid dosage form. By starting with a commonly available salt or free base of the active pharmaceutical ingredient, which is subsequently converted and incorporated in-situ as a tannate salt complex, the invention provides an efficient and reproducible method to manufacture liquid or semi-solid products containing tannate salt complexes as active ingredients.

The process provides the addition of the active ingredient to a dispersion of tannic acid to generate a tannate salt complex. The presence of the dispersing agent prevents the clumping and aggregation of the tannate salt complex formed. Without further treatment, excipients such as thickening, suspending, coloring, sweetening and flavoring agents are therefore added to water under stirring, to form a dispersion. Preservatives, pH adjusting and anti-caking agents are added to suitable solvent under stirring to form a dispersion. After combining the dispersions a suspension dosage form, at a pH of 3.5–8.0 is the final result.

By forming a suspension of the tannate salt complex of the active, the process provides a dosage form, which affords a sustained release of the active pharmaceutical ingredients over prolonged intervals of time, thereby improving patient compliance factors.

DETAILED DESCRIPTION OF THE INVENTION

The present invention involves a novel manufacturing process for the preparation of liquid or semi-solid dosage forms containing a tannate salt complex of active pharmaceutical ingredients (API). This includes a conversion process which includes the steps of mixing a dispersing agent and tannic acid in a suitable solvent to generate a mixture in liquid form. The API as a salt or in the free base form is combined with the dispersing agent/tannic acid mixture to generate the tannate salt complex. The presence of the dispersing agent prevents the clumping and aggregation of the tannate salt complex formed and promotes uniformity in the solution. The conversion process requires the presence of basic functional groups such as amines and sulfoxides in the molecular structure of the API. The formation of the tannate salt is by reaction of amine groups (in the 1°, 2°, 3°, 4°, or amphoteric functional states) or of the other basic functional groups with tannic acid. The amount and ratio of dispersing agent and tannic acid, required for the completion of the reaction, is determined by the molecular configuration and concentration of the API.

Tannate salt complexes of active ingredients have been found to have better organoleptic properties such as taste, in comparison to other salts or free base forms. In addition, the tannate salt complex of the active is a significantly larger molecule, which affords absorption of the active over prolonged intervals of time, reducing the frequency of administration and thereby improves patient compliance factors.

Because of the large tannate molecule, the percentage of antihistamine or decongestant free base within the tannate salt is significantly lower than that in other salt forms such as the hydrochloride or maleate. The presence of low active percentages and the variable purity of the commercially available tannate salts leads to the stoichiometry of the active free base to tannic acid in the tannate salts to be different from batch to batch. This could cause significant dosing and processing problems during manufacture and increase the likelihood that commercially available pharmaceutical products contain variable and in some instances sub-therapeutic levels of said active drug substances. Therefore, it would be desirable if pharmaceutical compositions containing tannate salts of active ingredients could be prepared with reduced variability in active drug content and increased certainty that the actives are delivered within the therapeutic range.

By starting with a known amount of commonly available salt or the free base form of the API, which is subsequently converted and incorporated in-situ as a tannate salt, the invention provides an efficient and reproducible method to manufacture products containing tannate salts as active ingredients. Since the tannate salt of the API is generated and incorporated in-situ into the dosage form during the manufacturing process, the purification and drying steps required for the isolation of the tannate salt are eliminated and the stoichiometry of the tannate salt is uniform from batch to batch.

The active pharmaceutical ingredients (API) are selected from the group as follows:

Antihistamines:

(1) Carbinoxamine
(2) Chlorpheniramine (3) Pyrilamine
(4) Pheniramine
(5) Phenindamine
(6) Diphenhydramine
(7) Bromodiphenhydramine
(8) Bromphenirmaine
(9) Loratadine
(10) Desloratadine
(11) Fexofenadine
(12) Cetirizine
(13) Hydroxyzine
(14) Promethazine
(15) Acrivastine
(16) Triprolidine
(17) Meclizine
(18) Dimenhydrinate
(19) Triplennamine
(20) Doxylamine
(21) Diphenylpyrilamine
(22) Trimeprazine
(23) Chlorcylizine Antitussives:

(1) Carbetapentane
(2) Dextromethorphan
(3) Diphenhydramine
(4) Codeine
(5) Hydrocodone
(6) Oxycodone
(7) Morphine Decongestants:

(1) Phenylephrine
(2) Pseudoephedrine
(3) Ephedrine
(4) Diphenhydramine
(5) Cyproheptadine
(6) Phenyltoloxamine
(7) Clemastine Anticholinergics:

(1) Methscopolamine.

The active pharmacologic ingredients are used as the free bases or as salts having anionic functional groups such as bitartrate, maleate, citrate, chloride, bromide, acetate and sulfate. The source of the tannic acid is natural or synthetic.

The preferred dispersing agent is chosen from the group such as magnesium aluminum silicate, xanthan gum and cellulose compounds. The thickening agents employed include kaolin, pectin, xanthan gum and cellulose compounds. One preferred antihistamines decongestant combination is pyrilamine and phenylephrine. Another preferred antihistamines decongestant combination is carbetapentane and chlorpheniramine.

Tannate suspension products are the therapeutic preparations containing active ingredients as tannate salt complexes. The therapeutic preparations containing antihistamines, antitussives, anticholinergics and decongestants are indicated for relief of nasal congestion such as sinusitis, rhinitis and hay fever.

Typical combinations contain 30 mg of Carbetapentane tannate, 4 mg of Chlorpheniramine tannate and 5 mg of Phenylephrine tannate, as active ingredients; another contains 30 mg of Pyrilamine tannate and 5 mg of Phenylephrine tannate; another contains 12.5 mg of Pyrilamine tannate, 5 mg of Phenylephrine tannate and 2 mg of Chlorpheniramine tannate as active ingredients; another contains 75 mg of Pseudoephedrine tannate and 25 mg of Diphenhydramine tannate.

The excipients commonly used in the formulations are as follows: sucrose, saccharin sodium and artificial flavor as flavoring agents, kaolin, pectin, xanthan gum, magnesium aluminum silicate (referred to as MAS), as thickening and anti-caking agents, glycerin as a co-solvent, sodium citrate, sodium phosphate monobasic and dibasic, citric acid, sodium benzoate and benzoic acid as a pH adjusting and buffering agents, methylparaben as a preservative, FD&C Red No. 40 and FD&C Blue No. 1 as coloring agents and purified water.

Among the actives used, carbetapentane was obtained as the citrate; phenylephrine, pseudoephedrine and diphenhydramine were obtained as the hydrochloride; the pyrilamine and chlorpheniramine were obtained as maleate salts.

The salts of the active ingredients are preferably dissolved in purified water. However, other pharmaceutically acceptable liquids can be substituted for water such as isopropyl alcohol, ethanol, glycerin, propylene glycol, mineral oil or mixtures thereof. This leads to the dissociation of the salt into its free base and conjugate acid forms. Another solution containing excess tannic acid in purified water is prepared. While stirring at low speeds, the solution of the salt is added in small portions to the tannic acid solution. Because of the presence of excess tannic acid, the free base form reacts with the tannic acid to form the tannate salt complex. Since the tannate salt complex formed is larger in size and has low solubility in purified water, it is usually precipitated out of the solution.

The development of the process for the conversion of active ingredients to the tannate salt complexes is described below. The salt or free base of the active ingredients is dissolved in purified water or other pharmaceutically acceptable liquid. Purified water is taken in a 600 ml beaker and stirred. While stirring, MAS is added in small portions to obtain a dispersion. Once the MAS is dispersed, tannic acid is added to the mixture and stirred to form a uniform dispersion. Three different batches of the MAS/tannic acid dispersion in purified water are prepared for each active. In the three batches, the amount of tannic acid used is varied from an amount equal to that of the free base, two times that of the free base and three times that of the free base, present in the initial salt solution. The active ingredient solution is then added in small portions, under light stirring, to the MAS/tannic acid dispersion. After all of the solution is added, the volume is made up to 250 ml with purified water and stirring is continued for a period of ten minutes. The MAS is used in this step to serve as an adherent or a solid support for the tannic acid molecules to facilitate the conversion process. In addition, it also prevents the clumping of the tannate salt formed, which aides in the isolation of the precipitate of the tannate salt complex formed from the solution. The dispersion containing the tannate salt complex is transferred to the suspending medium.

The salt solutions of carbetapentane, chlorpheniramine, pseudoephedrine, pyrilamine and diphenhydramine after addition to the MAS/tannic acid dispersion result in formation of copious amounts of precipitate at all three concentrations of tannic acid. However, in the case of phenylephrine, the tannate salt complex shows partial solubility in purified water.

The above batches are assayed for the formation of the tannate salt complex. For all the actives, it is found that maximum conversion (greater than 97%) is achieved when tannic acid is used at three times the amount of the free base and so is chosen as the amount to be used in the final formulation.

The conversions of the actives prepared are then transferred to suspension vehicles without isolation or purification. Typical suspension vehicles are prepared comprising excipients such as kaolin/pectin or xanthan gum as thickening agents. In addition, the suspending vehicles also consist of sweetening, flavoring, coloring, pH-adjusting and buffering agents, preservatives and co-solvents. The conversions of the actives are found to be viscous (3000–5000 cps). They are transferred to the suspending medium by pouring. The precipitate formed during the conversion is found to adhere slightly to the walls of the container and is scraped into the suspending medium using a spatula. Purified water is used to wash the remainder of the material into the suspending medium. The conversions show significantly less adhesion to stainless steel containers than glass containers.

The Examples performed are as mentioned below. In all the Examples, the active ingredient is converted in-situ into the tannate salt complex and then added to the suspension. The conversion process yields insoluble and soluble tannate salt complexes of the active ingredients. The tannate salt complexes obtained from the conversion step are transferred without purification or isolation in suitable suspending vehicles of kaolin/pectin or xanthan gum as thickening agents.

EXAMPLE 1

Formation of the Insoluble Tannate Salt Complex by the Conversion Process

The active solution of carbetapentane citrate is prepared by dissolving 24.4 g of carbetapentane citrate into 60 mL of water. 530 ml of purified water is placed in a mixing tank and 53.7 g of MAS is added in small portions while mixing the water to form a dispersion. Once the dispersion is uniform and lump-free, 46.7 g of tannic acid (TA), (three times that of the free base of the active), is folded into the dispersion using a planetary mixer with a sweep blade. The sweeping action to disperse the tannic acid is found to significantly simplify the process by keeping the tannic acid particles from clumping and providing greater uniformity of the dispersion. The salt solution is then added in small portions, while continuing to stir the MAS/tannic acid dispersion using the planetary mixer. After all of the salt solution is added, the weight is made up to 800 g with purified water. Mixing is continued and 5 g samples of the conversion after ten, twenty and thirty minutes of mixing are taken in a centrifuge tube. The samples are subsequently centrifuged at 6500 rpm and the resulting supernatant solution is assayed for the presence of active. At the end of thirty minutes, a 10 g sample of the conversion is taken for assay of the actives. Similarly, the conversions of the other active ingredients are performed in like manner and the weights of the materials are as shown in the table below.

1. Carbetapentane

| Amt. of Drug (g) | Amt. of water (g) (Salt solution) | Amt. of MAS (g) | Amt. of TA (g) | Amt. of water (g) (MAS/TA Disp.) | Total conversion (g) |
|---|---|---|---|---|---|
| 24.4 | 60.0 | 53.7 | 46.7 | 530.0 | 800.0 |

2. Chlorpheniramine

| Amt. of Drug (g) | Amt. of water (g) (Salt solution) | Amt. of MAS (g) | Amt. of TA (g) | Amt. of water (g) (MAS/TA Disp.) | Total conversion (g) |
|---|---|---|---|---|---|
| 15.51 | 60.0 | 43.44 | 32.76 | 600.00 | 800.00 |

3. Pyrilamine

| Amt. of Drug (g) | Amt. of water (g) (Salt solution) | Amt. of MAS (g) | Amt. of TA (g) | Amt. of water (g) (MAS/TA Disp.) | Total conversion (g) |
|---|---|---|---|---|---|
| 24.83 | 60.00 | 61.50 | 55.00 | 550.00 | 800.00 |

The results obtained from the above samples are as shown below:

| Active | Salt Soln (mg/g) | Assay (% Dissolved) 10 mins | 20 mins | 30 mins | Assay (final sample) (mg/g) |
|---|---|---|---|---|---|
| Carbetapentane | 299.1 | 0.08 | 0.08 | 0.09 | 30.3 (30.5)* |
| Chlorpheniramine | 216.6 | 0.12 | 0.13 | 0.14 | 19.9 (19.4)* |
| Pyrilamine | 290.9 | 0.10 | 0.10 | 0.11 | 29.2 (31.0)* |

*Number in parenthesis indicates the theoretical amount of active in mg/g

The formation of the insoluble tannate salt complex of the active, as explained earlier, leads to the precipitation of the tannate salt from solution as evidenced from the results above for carbetapentane, pyrilamine, and chlorpheniramine. For all three actives, the amount of active ingredient present in solution at the ten, twenty and thirty minute mixing times is <0.2%.

EXAMPLE 2

Formation of the Partially Soluble Tannate Salt Complex by the Conversion Process To illustrate the solubility of the tannate salt complex, and to obtain accurate values for the percent active dissolved, two experiments are performed. In the first experiment, a salt solution of phenylephrine HCl is added to a MAS/tannic acid dispersion and the amount of active ingredient present in solution at the ten, twenty and thirty minute mixing times, is more than 47.0%.

Expt.-1 Phenylephrine HCl

| Amt. of Drug (g) | Amt. of water (g) (Salt solution) | Amt. of MAS (g) | Amt. of TA (g) | Amt. of water (g) (MAS/TA Disp.) | Total conversion (g) |
| --- | --- | --- | --- | --- | --- |
| 12.5 | 40.0 | 43.8 | 30.9 | 600.0 | 800.0 |

Expt-I (Results)

| | Salt Soln | Assay (% Dissolved) | | | Assay (final sample) |
| --- | --- | --- | --- | --- | --- |
| Active | (mg/g) | 10 mins | 20 mins | 30 mins | (mg/g) |
| Phenylephrine | 276.5 | 37.14 | 47.6 | 47.6 | 16.8 (18.1)* |

*Number in parenthesis indicates the theoretical amount of active in mg/g.

In a second experiment commercial phenylephrine tannate raw material is added to a dispersion of MAS and mixed for a period of ten minutes. The results obtained are as below:

Expt-II-Phenylephrine Tannate

| Amt. of Drug (g) | Amt. of water (g) (Salt solution) | Amt. of MAS (g) | Amt. of TA (g) | Amt. of water (g) (MAS/TA Disp.) | Total conversion (g) |
| --- | --- | --- | --- | --- | --- |
| 1.56 | n/a | 5.48 | n/a | 85.00 | 100.0 |

Expt-II (Results)

| Active | 10 minute mixing sample Amt. (mg/g) | 10 minute mixing sample % Dissolved | Assay (final sample) (mg/g) |
| --- | --- | --- | --- |
| Phenylephrine | 9.5 | 25.1 | 37.8 (40.6)* |

Phenylephrine HCl is freely soluble (about 100.0% soluble) in water. From the results for Expt-I, it can be seen that the tannate salt complex is 57% soluble in water. This is further illustrated by the results from Expt-II which show that at least 25.0% of the commercially available tannate salt complex is soluble.

EXAMPLE 3

Formation of the Insoluble Tannate Salt Complex by the Conversion Process Using Organic Solvents The active solution of Dextromethorphan hydrobromide is prepared by dissolving 1.180 g of drug into 85:15 mixture of purified water and ethanol. 400 mL of purified water was taken in a 1 L mixing tank and 2.685 g of MAS is added in small portions while mixing the water for forming a dispersion. Once the dispersion is uniform and lump-free, 2.722 g of tannic acid (TA) (three times that of the free base of the active) is folded into the dispersion using a planetary mixer with a sweep blade. The sweeping action to disperse the tannic is found to significantly simplify the process by keeping the tannic acid particles from clumping and providing greater uniformity of the dispersion. The salt solution is then added in small portions, while continuing to stir the MAS/tannic acid dispersion using the planetary mixer. After all of the salt solution is added, the weight is made up to 500 g with purified water.

1. Dextromethorphan

| Amt. of Drug (g) | Amt. of water/ethanol (g) (Salt solution) | Amt. of MAS (g) | Amt. of TA (g) | Amt. of water (g) (MAS/TA Disp.) | Total conversion (g) |
| --- | --- | --- | --- | --- | --- |
| 1.180 | 51.180 | 2.685 | 2.726 | 405.411 | 500 |

EXAMPLE 4

Formation of the Tannate Salt Complex Using the Free Base of the Active Ingredient in the Conversion Process The active solution of brompheniramine is prepared by dissolving 23.538 g of drug into 100 mL of purified water. 500 mL of purified water is taken in a 1 L mixing tank and 2.5 g of MAS is added in small portions while mixing the water to form a dispersion. Once the dispersion is uniform and lump-free, 70.614 g of tannic acid (TA), (three times that of the free base of the active), is folded in to the dispersion using a planetary mixer with a sweep blade. The sweeping action to disperse the tannic acid is found to significantly simplify the process by keeping the tannic acid particles from clumping and providing greater uniformity of the dispersion. The salt solution is then added in small portions, while continuing to stir the MAS/tannic acid dispersion using the planetary mixer. After all of the salt solution is added, the weight is made up to 800 g with purified water.

1. Brompheniramine

| Amt. of Drug (g) | Amt. of water (g) (Salt solution) | Amt. of MAS (g) | Amt. of TA (g) | Amt. of water (g) (MAS/TA Disp.) | Total conversion (g) |
| --- | --- | --- | --- | --- | --- |
| 23.538 | 100 | 25.000 | 70.614 | 595.614 | 800 |

EXAMPLE 5

Preparation of a Suspension with Kaolin/pectin as Thickening Agents

| | % w/v | mg/5 mL |
| --- | --- | --- |
| Pyrilamine Tannate | 0.250% | 12.500 |
| Phenylephrine Tannate | 0.100% | 5.000 |
| Chlorpheniramine Tannate | 0.040% | 2.000 |
| Saccharin Sodium | 0.05% | 0.003 |
| Sucrose | 10.00% | 0.500 |
| Glycerin | 7.500% | 0.375 |
| Magnesium aluminum Silicate | 1.750% | 0.088 |
| Kaolin | 1.600% | 0.080 |
| Pectin | 1.750% | 0.088 |
| Methylparaben | 0.200% | 0.010 |
| Benzoic Acid | 0.100% | 0.005 |
| FD&C Red No. 40 | 0.020% | 0.001 |
| Strawberry Flavor | 0.050% | 0.003 |
| Purified Water | qs to volume | N/A |

The saccharin sodium, sucrose, kaolin and a part of the MAS are dispersed in purified water in stainless steel mixing tank, using a suitable stirrer. The coloring agent and the artificial strawberry flavor are then added and mixing is continued to generate the suspending medium.

The pyrilamine maleate is dissolved in purified water. In another mixing tank MAS and tannic acid are dispersed in purified water using a mixer. Once a uniform dispersion is achieved, the solution of the drug is poured in small portions to the tank while stirring. After all of the solution is transferred, stirring is continued for ten minutes. The contents of the tank are then transferred to the suspending medium.

The phenylephrine HCl is dissolved in purified water. In another mixing tank, MAS and tannic acid are dispersed in purified water using a mixer. Once a uniform dispersion is achieved, the solution of the drug is poured in small portions to the tank while stirring. After all of the solution is transferred, stirring is continued for ten minutes. The contents of the tank are then transferred to the suspending medium.

The pectin is dispersed in glycerin in a mixing tank using a mixer. The benzoic acid and methylparaben are then dispersed in the glycerin mixture in the tank. The glycerin mixture is added to the suspending medium containing the active ingredients and mixed to get a uniform dispersion.

Finally, purified water is added to make up to the suspension to the required volume and mixed to obtain an elegant product.

EXAMPLE 6

Preparation of a Suspension with Xanthan Gum as Thickening Agent

|  | % w/v | mg/5 mL |
| --- | --- | --- |
| Pseudoephedrine Tannate | 1.500% | 75.000 |
| Diphenhydramine Tannate | 0.500% | 25.000 |
| Saccharin Sodium | 0.300% | 0.015 |
| Sucrose | 10.000% | 0.500 |
| Glycerin | 7.500% | 0.375 |
| Magnesium Aluminum Silicate | 0.800% | 0.040 |
| Xanthan gum | 0.520% | 0.026 |
| Dibasic sodium phosphate | 1.000% | 1.050 |
| Methylparaben | 0.200% | 0.010 |
| Sodium benzoate | 0.100% | 0.005 |
| FD&C Red No. 40 | 0.040% | 0.002 |
| Strawberry Flavor | 0.500% | 0.025 |
| Purified Water | qs to volume | N/A |

The sodium phosphate dibasic is dissolved in purified water in a suitable stainless steel mixing tank. The MAS, followed by xanthan gum, is dispersed in the solution. The coloring agent FD&C Red No. 40 and the artificial strawberry flavor are then added and mixed to generate the suspending medium. In a separate mixing tank, the MAS and tannic acid are dispersed in water using a suitable stirrer. Mixing is continued until a uniform dispersion is achieved.

Pseudoephedrine HCl is dissolved in purified water. While stirring the MAS/tannic acid dispersion in the mixing tank at low speed, the pseudoephedrine HCl solution is transferred in small portions to the dispersion. Stirring is continued for a minimum of ten minutes. After mixing, the contents of the tank are transferred to the suspending medium and mixed for a period of five minutes. Similarly, the chlorpheniramine maleate is converted to the tannate salt and transferred to the suspending medium.

The sodium benzoate and methylparaben are dispersed in glycerin in a mixing tank using a suitable mixer. The glycerin mixture is then added to the suspending medium and mixed to achieve a uniform dispersion. Finally, purified water is added to make up the suspension to the required volume.

EXAMPLE 7

Preparation of a Suspension Using HPMC and Propylene Glycol in the Conversion Step

|  | % w/y | mg/5 mL |
| --- | --- | --- |
| Pyrilamine Tannate | 0.250% | 12.500 |
| Phenylephrine Tannate | 0.100% | 5.000 |
| Chlorpheniramine Tannate | 0.040% | 2.000 |
| Saccharin Sodium | 0.05% | 2.500 |
| Sucrose | 10.00% | 500.000 |
| Glycerin | 7.500% | 375.000 |
| Propylene Glycol | 2.000% | 100.000 |
| HPMC | 1.750% | 87.500 |
| Kaolin | 1.600% | 80.000 |
| Pectin | 1.750% | 87.500 |
| Methylparaben | 0.200% | 10.000 |
| Benzoic Acid | 0.100% | 5.000 |
| FD&C Red #40 | 0.020% | 1.000 |
| Strawberry Flavor | 0.050% | 3.000 |
| Purified Water | qs to volume | n/a |

The saccharin sodium, sucrose, kaolin and a part of the HPMC are dispersed in purified water in stainless steel mixing tank, using a suitable stirrer. The coloring agent and the artificial strawberry flavor are then added and mixing is continued to generate the suspending medium.

The pyrilamine maleate is dissolved in purified water. In another mixing tank HPMC and tannic acid are dispersed in 75:25 purified water/propylene glycol mixture using a mixer. Once a uniform dispersion is achieved, the solution of the drug is poured in small portions to the tank while stirring. After all of the solution is transferred, stirring is continued for ten minutes. The contents of the tank are then transferred to the suspending medium. The phenylephrine HCl is dissolved in purified water. In another mixing tank, HPMC and tannic acid are dispersed in 75:25 purified water/propylene glycol mixture using a mixer. Once a uniform dispersion is achieved, the solution of the drug is poured in small portions to the tank while stirring. After all of the solution was transferred, stirring is continued for ten minutes. The contents of the tank are then transferred to the suspending medium. The pectin is dispersed in glycerin in a mixing tank using a mixer. The benzoic acid and methylparaben are then dispersed in the glycerin mixture in the tank. The glycerin mixture is added to the suspending medium containing the active ingredients and mixed to provide a uniform dispersion.

Finally, purified water is added to make up to the suspension to the required volume and mixed to obtain an elegant product.

The foregoing is considered as illustrative only of the principles of the invention. Further, various equivalents to the ingredients may be substituted without departing from the scope thereof and it is desired, therefore, that only such limitations shall be placed thereon as are imposed by the prior art and which are set forth in the appended claims.

What is claimed is:

1. A manufacturing process for the in-situ conversion and incorporation of a salt or free base of an active pharmaceutical ingredient selected from the group consisting of an antihistamine, a decongestant, an antitussive and an anticholinergic for incorporation into a therapeutic liquid or semi-solid dosage form, the process comprising the steps of:

(a) dissolving the salt or free base of the active pharmaceutical ingredient in a pharmaceutically acceptable liquid to form a solution; at (b) separately adding a dispersing agent comprising magnesium aluminum silicate, xanthan gum or mixtures thereof and tannic acid to a pharmaceutically acceptable liquid to form a dispersion;

(c) transferring the solution from step (a), to the dispersion in step (b) to form a precipitate of a tannate salt complex of the active pharmaceutical ingredient; and (d) combining the tannate salt complex of the active pharmaceutical ingredient without isolation or purification with a pharmaceutically acceptable excipient to generate a therapeutic dosage form.

2. The process according to claim 1 wherein the antihistamine active pharmaceutical ingredient is selected from the group consisting of:

Carbinoxamine,
Chlorpheniramine,
Pyrilamine,
Pheniramine,
Phenindamine,
Diphenhydramine,
Bromodiphenhydramine
Brompheniramine,
Loratadine,
Desloratadine,
Fexofenadine,
Cetirizine,
Hydroxyzine,
Promethazine,
Acrivastin,
Triprolidine,
Meclizine,
Dimenhydrinate,
Triplermamine
Doxylamine,
Diphenylpyrilamine,
Trimeprazine; and
Cholorcylizine.

3. The process according to claim 1 wherein the antitussive active pharmaceutical ingredient is selected from the group consisting of.

Carbetapentane,
Dextromethorphan,
Diphenhydramine,
Codeine,
Hydrocodone,
Oxycodone; and
Morphine.

4. The process according to claim 1 wherein the decongestant active pharmaccutical ingredient is selected from the group consisting of:

Phenylephrine,
Pseudoephedrine,
Ephedrine,
Diphenhydramine,
Cyproheptadine,
Phenyltoloxamine, and
Clemastine.

5. The process according to claim 1 wherein the antihistamine and decongestant active ingredients are provided as the bitartrate, maleate, citrate, chloride, bromide, acetate or sulfate salt.

6. The process according to claim 1 wherein the tannic acid provided in step (b) is natural or synthetic.

7. The process according to claim 1 wherein the pharmaceutically acceptable liquid in steps (a) and (b) is selected from the group consisting of purified water, isopropyl alcohol, ethanol, glycerin, propylene glycol, mineral oil and mixtures thereof.

8. The process according to claim 7 wherein the pharmaceutically acceptable liquid in steps (a) and (b) is purified water.

9. The process according to claim 1 wherein the pharmaceutically acceptable excipient is selected from a group consisting of sucrose, saccharin sodium, an artificial flavor, kaolin, pectin, xanthan gum, magnesium aluminum silicate, glycerin, sodium citrate, sodium phosphate monobasic, sodium phosphate dibasic, citric acid, sodium benzoate, benzoic acid, methylparaben, a coloring agent and mixtures thereof.

* * * * *

UNITED STATES PATENT AND TRADEMARK OFFICE
CERTIFICATE OF CORRECTION

PATENT NO. : 6,869,618 B2
DATED : March 22, 2005
INVENTOR(S) : Kiel et al.

It is certified that error appears in the above-identified patent and that said Letters Patent is hereby corrected as shown below:

Column 11,
Line 3, after the semicolon, please delete the word "at".
Line 37, please replace "Acrivastin" with -- Acrivastine --.
Line 38, please replace "Triplermamine" with -- Triplennamine --.
Line 46, please replace "Cholorcylizine" with -- Chlorcylizine --.

Signed and Sealed this

Twenty-fourth Day of May, 2005

JON W. DUDAS
*Director of the United States Patent and Trademark Office*